(12) United States Patent
Ono et al.

(10) Patent No.: US 8,435,778 B2
(45) Date of Patent: May 7, 2013

(54) GENE ENCODING LIGNAN METHYLTRANSFERASE AND USE THEREOF

(75) Inventors: Eiichiro Ono, Osaka (JP); Toshiaki Umezawa, Kyoto (JP); Takefumi Hattori, Kyoto (JP); Shiro Suzuki, Kyoto (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

(21) Appl. No.: 13/642,911

(22) PCT Filed: May 13, 2010

(86) PCT No.: PCT/JP2010/058127
§ 371 (c)(1),
(2), (4) Date: Oct. 23, 2012

(87) PCT Pub. No.: WO2011/142019
PCT Pub. Date: Nov. 17, 2011

(65) Prior Publication Data
US 2013/0040348 A1 Feb. 14, 2013

(51) Int. Cl.
*C12N 9/14* (2006.01)
*C12N 15/00* (2006.01)
*C12N 1/20* (2006.01)
*C07K 1/00* (2006.01)
*C07H 21/04* (2006.01)

(52) U.S. Cl.
USPC .................. 435/195; 435/252.3; 435/320.1; 536/23.2; 530/350

(58) Field of Classification Search .......... 536/23.2; 530/350; 435/6, 252.3, 320.1
See application file for complete search history.

(56) References Cited

U.S. PATENT DOCUMENTS
2009/0241226 A1  9/2009  Ono
2010/0058498 A1  3/2010  Apuya et al.

FOREIGN PATENT DOCUMENTS
JP       2007-259789    10/2007
WO      2008-069878    6/2008

OTHER PUBLICATIONS

Masaaki Nakai et al., "Novel Antioxidative Metabolites in Rat Liver with Ingested Sesamin", J. Agric. Food Chem. 2003, 51, pp. 1666-1670.
Nobuo Tsuruoka et al., "Modulating Effect of Sesamin, a Functional Lignan in Sesame Seeds, on the Transcription Levels of Lipid- and Alcohol-Metabolizing Enzymes in Rat Liver: A DNA Microarray Study", Biosci. Biotechnol. Biochem., 69 (1), 2005, pp. 179-188.
Laurence B. Davin et al., "An historical perspective on lignan biosynthesis: Monolignol, allylphenol and hydroxycinnamic acid coupling and downstream metabolism", Phytochemistry Reviews 2: 2003, pp. 257-288.
Akio Noguchi et al., "Sequential glucosylation of a furofuran lignan, (+)-sesaminol, by Sesamum indicum UGT71A9 and UGT94D1 glucosyltransferases", The Plant Journal (2008) 54, pp. 415-427.
Norikazu Sakakibara et al., "Biosynthesis of yatein in *Anthriscus sylvestris*", Org. Biomol. Chem., 2003, 1, pp. 2474-2485.
Toshiaki Umezawa et al., "A novel *O*-methyltransferase catalyzing a regioselective methylation of lignan", Dai 49 Kai Lignin Toronkai Koenshu, Oct. 20, 2004, pp. 33-36.
Shuiqin Wu et al., "The Key Role of Phloroglucinol *O*-Methyltransferase in the Biosynthesis of *Rosa chinensis* Volatile 1,3,5-Trimethoxybenzene", Plant Physiology, May 2004, vol. 135, pp. 95-102.
Shiro Suzuki, "Stereochemical Diversity in Lignan Biosynthesis and Establishment of Norlignan Biosynthetic Pathway", Wood Research, 2002, No. 89, pp. 52-60.
International Search Report and Written Opinion dated Jun. 8, 2010 in PCT/JP2010/058127 filed May 13, 2010.

*Primary Examiner* — Maryam Monshipouri
(74) *Attorney, Agent, or Firm* — Drinker Biddle & Reath LLP (57) ABSTRACT

The present invention provides an enzyme having an activity of transferring a methyl group to lignans (a lignan methylation activity) (e.g., a protein comprising the amino acid sequence of SEQ ID NO: 2 or variants thereof); a gene encoding the enzyme (e.g., a polynucleotide comprising the nucleotide sequence of SEQ ID NO: 1 or variants thereof); a method for producing methylated lignans using the gene; and so on.

13 Claims, 5 Drawing Sheets

Fig. 1: GC Charts of Authentic Samples

Fig. 2: MS Spectra of Authentic Samples

Fig. 3: Predicted Structures of Fragment Ions

Fig. 4: GC Charts of Enzymatic Reaction Solutions of AsOMT116

Fig. 5: MS Spectra of Enzymatic Reaction Solution of AsOMT116

SEQUENCE LISTING

```
<160> NUMBER OF SEQ ID NOS: 12

<210> SEQ ID NO 1
<211> LENGTH: 1107
<212> TYPE: DNA
<213> ORGANISM: Anthrissus sylvestris
<220> FEATURE:
<221> NAME/KEY: misc_feature
<222> LOCATION: (1)..(1107)
<223> OTHER INFORMATION: AsOMT116
<220> FEATURE:
<221> NAME/KEY: CDS
<222> LOCATION: (1)..(1107)

<400> SEQUENCE: 1 atg tct aaa caa gat caa gat gcc act gaa ttc aca agg gtg ctg cag       48
Met Ser Lys Gln Asp Gln Asp Ala Thr Glu Phe Thr Arg Val Leu Gln
1               5                   10                  15 gta agt ggt ggc ata att ctt gga atg gta ttg aaa gct gct gtt gag       96
Val Ser Gly Gly Ile Ile Leu Gly Met Val Leu Lys Ala Ala Val Glu
            20                  25                  30 ttt aat ctt ttc gag atc atg gcc aat gct gct gct gtt gat gga gct      144
Phe Asn Leu Phe Glu Ile Met Ala Asn Ala Ala Ala Val Asp Gly Ala
        35                  40                  45 tct cct ttc gga gat gat gct aag aag ttg tct agt gat gat att gta      192
Ser Pro Phe Gly Asp Asp Ala Lys Lys Leu Ser Ser Asp Asp Ile Val
    50                  55                  60 gct cat ctt ccc aca caa aat cct gca gct act gca atg ctg gag cga      240
Ala His Leu Pro Thr Gln Asn Pro Ala Ala Thr Ala Met Leu Glu Arg
65                  70                  75                  80 att ctt cgg ttt ctg tct gct cat tcc ttt ctt acc agg acc gta gta      288
Ile Leu Arg Phe Leu Ser Ala His Ser Phe Leu Thr Arg Thr Val Val
                85                  90                  95 gct gga gaa ggt ggc cag gaa cag agt ttg tat ggt cta gaa agt att      336
Ala Gly Glu Gly Gly Gln Glu Gln Ser Leu Tyr Gly Leu Glu Ser Ile
            100                 105                 110 tgc aag aat tac att cct gat caa gat ggt gtt tca ttt gct cct tta      384
Cys Lys Asn Tyr Ile Pro Asp Gln Asp Gly Val Ser Phe Ala Pro Leu
        115                 120                 125 ttg gtt atg ctt cat gac aaa gtt atc atc gat tct ttg ttg tgc ttg      432
Leu Val Met Leu His Asp Lys Val Ile Ile Asp Ser Leu Leu Cys Leu
```

```
                130                 135                 140
aaa gat gca ctt ctt gag gga ggt att ccg ttt aac aag gct cat gat    480
Lys Asp Ala Leu Leu Glu Gly Gly Ile Pro Phe Asn Lys Ala His Asp
145                 150                 155                 160 ggc atg gat gca ttt gaa tac cct gca ata gac agc aga ttc aat gac    528
Gly Met Asp Ala Phe Glu Tyr Pro Ala Ile Asp Ser Arg Phe Asn Asp
                165                 170                 175 gtt ttc aat caa gca atg tac aac cac acc act tta atc atg aag aag    576
Val Phe Asn Gln Ala Met Tyr Asn His Thr Thr Leu Ile Met Lys Lys
            180                 185                 190 att cta gaa gtt tac gct gga ttc gaa gaa ctc aca gag att gta gat    624
Ile Leu Glu Val Tyr Ala Gly Phe Glu Glu Leu Thr Glu Ile Val Asp
        195                 200                 205 gtt ggt ggt gga acc ggg gca aca cta gcc aaa atc atg tcc aaa tat    672
Val Gly Gly Gly Thr Gly Ala Thr Leu Ala Lys Ile Met Ser Lys Tyr
    210                 215                 220 cct cat atc agg gga atc aac ttc gat ttg cct cat gtc atc aag aac    720
Pro His Ile Arg Gly Ile Asn Phe Asp Leu Pro His Val Ile Lys Asn
225                 230                 235                 240 gcc cct cct tta gct ggt gtg gag cat gtg gga gga gat atg ttt gaa    768
Ala Pro Pro Leu Ala Gly Val Glu His Val Gly Gly Asp Met Phe Glu
                245                 250                 255 agt gtc ccg aaa gga gag gtc atc ttc atg aag tgg ata ctt cat gat    816
Ser Val Pro Lys Gly Glu Val Ile Phe Met Lys Trp Ile Leu His Asp
            260                 265                 270 tgg agc gat gga cac tgc tta aag ctt ttg cag aat tgc tgc aac tcc    864
Trp Ser Asp Gly His Cys Leu Lys Leu Leu Gln Asn Cys Cys Asn Ser
        275                 280                 285 ctt cca gaa tct ggc aag gtg ata att gta gaa tca ata gtg cca gag    912
Leu Pro Glu Ser Gly Lys Val Ile Ile Val Glu Ser Ile Val Pro Glu
    290                 295                 300 aat acg aac aca ggt tct tca tcg gaa tta agc aat gtc atg agc aat    960
Asn Thr Asn Thr Gly Ser Ser Ser Glu Leu Ser Asn Val Met Ser Asn
305                 310                 315                 320 gat atg gta atg ctg gca gta aat ccg gga gga aag gag agg agt atc   1008
Asp Met Val Met Leu Ala Val Asn Pro Gly Gly Lys Glu Arg Ser Ile
                325                 330                 335 aaa gaa ttt gag gca ttg gca aaa gaa tct gga ttc gcc acc gta gaa   1056
Lys Glu Phe Glu Ala Leu Ala Lys Glu Ser Gly Phe Ala Thr Val Glu
            340                 345                 350 ctc ata tgc agc gtc gct ata tat agt gtt cta gaa ttt cat aag aaa   1104
Leu Ile Cys Ser Val Ala Ile Tyr Ser Val Leu Glu Phe His Lys Lys
        355                 360                 365 gtg                                                                1107
Val
```

<210> SEQ ID NO 2
<211> LENGTH: 369
<212> TYPE: PRT
<213> ORGANISM: Anthrissus sylvestis

<400> SEQUENCE: 2

```
Met Ser Lys Gln Asp Gln Asp Ala Thr Glu Phe Thr Arg Val Leu Gln
1               5                   10                  15

Val Ser Gly Gly Ile Ile Leu Gly Met Val Leu Lys Ala Ala Val Glu
            20                  25                  30

Phe Asn Leu Phe Glu Ile Met Ala Asn Ala Ala Ala Val Asp Gly Ala
        35                  40                  45

Ser Pro Phe Gly Asp Asp Ala Lys Lys Leu Ser Ser Asp Ile Val
    50                  55                  60
```

```
Ala His Leu Pro Thr Gln Asn Pro Ala Thr Ala Met Leu Glu Arg
 65                  70                  75                  80

Ile Leu Arg Phe Leu Ser Ala His Ser Phe Leu Thr Arg Thr Val Val
                 85                  90                  95

Ala Gly Glu Gly Gly Gln Glu Gln Ser Leu Tyr Gly Leu Glu Ser Ile
            100                 105                 110

Cys Lys Asn Tyr Ile Pro Asp Gln Asp Gly Val Ser Phe Ala Pro Leu
            115                 120                 125

Leu Val Met Leu His Asp Lys Val Ile Ile Asp Ser Leu Leu Cys Leu
            130                 135                 140

Lys Asp Ala Leu Leu Glu Gly Gly Ile Pro Phe Asn Lys Ala His Asp
145                 150                 155                 160

Gly Met Asp Ala Phe Glu Tyr Pro Ala Ile Asp Ser Arg Phe Asn Asp
                165                 170                 175

Val Phe Asn Gln Ala Met Tyr Asn His Thr Thr Leu Ile Met Lys Lys
            180                 185                 190

Ile Leu Glu Val Tyr Ala Gly Phe Glu Glu Leu Thr Glu Ile Val Asp
            195                 200                 205

Val Gly Gly Gly Thr Gly Ala Thr Leu Ala Lys Ile Met Ser Lys Tyr
210                 215                 220

Pro His Ile Arg Gly Ile Asn Phe Asp Leu Pro His Val Ile Lys Asn
225                 230                 235                 240

Ala Pro Pro Leu Ala Gly Val Glu His Val Gly Gly Asp Met Phe Glu
                245                 250                 255

Ser Val Pro Lys Gly Glu Val Ile Phe Met Lys Trp Ile Leu His Asp
            260                 265                 270

Trp Ser Asp Gly His Cys Leu Lys Leu Leu Gln Asn Cys Cys Asn Ser
            275                 280                 285

Leu Pro Glu Ser Gly Lys Val Ile Ile Val Glu Ser Ile Val Pro Glu
            290                 295                 300

Asn Thr Asn Thr Gly Ser Ser Ser Glu Leu Ser Asn Val Met Ser Asn
305                 310                 315                 320

Asp Met Val Met Leu Ala Val Asn Pro Gly Gly Lys Glu Arg Ser Ile
                325                 330                 335

Lys Glu Phe Glu Ala Leu Ala Lys Glu Ser Gly Phe Ala Thr Val Glu
            340                 345                 350

Leu Ile Cys Ser Val Ala Ile Tyr Ser Val Leu Glu Phe His Lys Lys
            355                 360                 365

Val

<210> SEQ ID NO 3
<211> LENGTH: 22
<212> TYPE: DNA
<213> ORGANISM: Artificial Sequence
<220> FEATURE:
<223> OTHER INFORMATION: Primer (OMT Forward 1 primer)

<400> SEQUENCE: 3
ggaactctgg ttgatgttgg tg                                           22

<210> SEQ ID NO 4
<211> LENGTH: 23
<212> TYPE: DNA
<213> ORGANISM: Artificial Sequence
<220> FEATURE:
<223> OTHER INFORMATION: Primer (OMT Reverse 1 primer)
```

```
<400> SEQUENCE: 4
cgatgatgga ttcaattgca gga                                          23

<210> SEQ ID NO 5
<211> LENGTH: 22
<212> TYPE: DNA
<213> ORGANISM: Artificial Sequence
<220> FEATURE:
<223> OTHER INFORMATION: Primer (OMT Forward 2 primer)

<400> SEQUENCE: 5
tgaagacctt ggtggatgtt gg                                           22

<210> SEQ ID NO 6
<211> LENGTH: 24
<212> TYPE: DNA
<213> ORGANISM: Artificial Sequence
<220> FEATURE:
<223> OTHER INFORMATION: Primer (OMT Reverse 2 primer)

<400> SEQUENCE: 6
tatgaaatcc tttgaagccg gcag                                         24

<210> SEQ ID NO 7
<211> LENGTH: 21
<212> TYPE: DNA
<213> ORGANISM: Artificial Sequence
<220> FEATURE:
<223> OTHER INFORMATION: Primer (OMT Forward 3 primer)

<400> SEQUENCE: 7
tgaaggcctc acgtccttgg t                                            21

<210> SEQ ID NO 8
<211> LENGTH: 21
<212> TYPE: DNA
<213> ORGANISM: Artificial Sequence
<220> FEATURE:
<223> OTHER INFORMATION: Primer (OMT Reverse 3 primer)

<400> SEQUENCE: 8
tggaagccag ctcccttagc t                                            21

<210> SEQ ID NO 9
<211> LENGTH: 22
<212> TYPE: DNA
<213> ORGANISM: Artificial Sequence
<220> FEATURE:
<223> OTHER INFORMATION: Primer (OMT Forward 4 primer)

<400> SEQUENCE: 9
cgccagaatt gtgatgaagg ct                                           22

<210> SEQ ID NO 10
<211> LENGTH: 23
<212> TYPE: DNA
<213> ORGANISM: Artificial Sequence
<220> FEATURE:
<223> OTHER INFORMATION: Primer (OMT Reverse 4 primer)

<400> SEQUENCE: 10
gtaacgacta aacccgcctt cca                                          23

<210> SEQ ID NO 11
<211> LENGTH: 29
<212> TYPE: DNA
```

```
<213> ORGANISM: Artificial Sequence
<220> FEATURE:
<223> OTHER INFORMATION: Primer (AsOMTExp-116-F #481)

<400> SEQUENCE: 11
ggaattcgct agcatgtcta aacaagatc                                29

<210> SEQ ID NO 12
<211> LENGTH: 30
<212> TYPE: DNA
<213> ORGANISM: Artificial Sequence
<220> FEATURE:
<223> OTHER INFORMATION: Primer (AsOMTExp-116-R #482)

<400> SEQUENCE: 12
atttctcgag cactttctta tgaaattcta                               30
```

GENE ENCODING LIGNAN METHYLTRANSFERASE AND USE THEREOF

TECHNICAL FIELD

The present invention relates to an enzyme having a lignan methylation activity (an activity of transferring a methyl group to lignan), a gene encoding the same, a method for preparing methylated lignans using the gene, and so on.

BACKGROUND ART

Lignans are a class of plant secondary metabolites ubiquitously distributed in the plant kingdom (Non-Patent Document: Umezawa, T. (2003) Phytochem. Rev. 2, 371-390). Some lignans have useful biological activities and are used as drugs or health foods. For example, main furofuran-type lignans contained in *Sesamum indicum* of the family Pedaliaceae are known to have functions including antioxidative properties, improvement of lipid metabolism, protection of liver function, etc. and are commercially available (Non-Patent Document 1: Nakai, M., et al. (2003) J. Agri. Food Chem. 51, 1666-1670; Non-Patent Document 2: Tsuruoka, T. et al. (2005) Biosci. Biotech. Biochem. 69, 179-188).

On the other hand, podophyllotoxins, which are anti-tumor lignans of allyl tetralin lactone type contained in the root of Berberidaceae *Podophyllum peltatum* (American May apple), have a cell division inhibitory activity and are used as carcinostatic agents and for development of novel carcinostatic agents (Non-Patent Document 3: Ayres, D. C. and Loike, J. D. (1990) Lignans: Chemical Biological and Clinical Properties. Cambridge Univ. Press, Cambridge, U.K.). Also, numerous lignans are considered to be metabolized in vivo, after their uptake, into enterolactone which has a female sex hormone-like activity.

As such, the usefulness of lignans is becoming clear. In contrast, information of genes for catalytic enzymes in lignan biosynthesis is limited (Non-Patent Document 4: Davin, L. B. and Lewis, N. G. (2003) Phytochem. Rev. 2, 257-288).

Lignan biosynthesis has been studied mainly in *Forsythia intermedia*, Berberidaceae *Podophyllum peltatum* and *Linum usitatissimum*, and starts from pinoresinol which is a furofuran lignan synthesized through oxidative polymerization of coniferyl alcohol that is one of monolignols. It is shown in *Sesamum indicum* that pinoresinol is converted into sesamin by forming two methylenedioxy bridges in pinoresinol by cytochrome P450 enzyme CYP81Q1 and its metabolite sesaminol is further glucosylated (Non-Patent Document 5: Noguchi, A., et al (2008) Plant J. 54, 415-427).

In the biosynthesis pathway of lignans with a lactone ring, pinoresinols are metabolized by pinoresinol-lariciresinol reductases (PLR) to lariciresinol and then secoisolariciresinol (Non-Patent Document 4). Secoisolariciresinol is further converted into matairesinol by secoisolariciresinol dehydrogenase (SIRD).

The metabolic pathway of lignans with a lactone ring subsequent to matairesinol requires to go through a plurality of enzyme reactions to reach podophyllotoxin glycoside. However, some enzyme activities are merely reported but any execution enzyme has not been isolated (Non-Patent Document 6: Sakakibara, N., et al (2003) Org. Biomol. Chem. 1, 2474-2485).

*Anthrissus sylvestris* is known to contain lignans with a lactone ring such as yatein, podophyllotoxin, etc. in the leaves and roots. It is further demonstrated by administration experiments with labeled lignans that yatein is biosynthesized via thujaplicatin, 5-methylthujaplicatin and 4,5-dimethylthujaplicatin (Non-Patent Document 6).

Non-Patent Documents

Non-Patent Document 1: J. Agri. Food Chem. 51, 1666-1670 (2003)
Non-Patent Document 2: Biosci. Biotech. Biochem. 69, 179-188 (2005)
Non-Patent Document 3: Lignans: Chemical Biological and Clinical Properties. Cambridge Univ. Press, Cambridge, U.K. (1990)
Non-Patent Document 4: Phytochem. Rev. 2, 257-288 (2003)
Non-Patent Document 5: Plant J. 54, 415-427 (2008)
Non-Patent Document 6: Org. Biomol. Chem. 1, 2474-2485 (2003)

DISCLOSURE OF THE INVENTION

Problem to be Solved by the Invention

Under these circumstances, it has been desired to identify a novel enzyme associated with lignan biosynthesis and a gene encoding the same.

The present invention has been made in view of the circumstances described above, and provides an enzyme having a lignan methylation activity, a polynucleotide encoding the same, a vector comprising the polynucleotide, a transformant, a method for preparing a methylated lignan using the transformant, and so on.

(1) A polynucleotide selected from the group consisting of (a) to (d) below:
(a) a polynucleotide comprising the nucleotide sequence of SEQ ID NO: 1;
(b) a polynucleotide encoding a protein consisting of the amino acid sequence of SEQ ID NO: 2;
(c) a polynucleotide encoding a protein consisting of an amino acid sequence wherein 1 to 50 amino acids are deleted, substituted, inserted and/or added in the amino acid sequence of SEQ ID NO: 2, and having a lignan methylation activity; and,
(d) a polynucleotide encoding a protein having an amino acid sequence having at least 70% identity to the amino acid sequence of SEQ ID NO: 2, and having a lignan methylation activity.

(1a) A polynucleotide selected from the group consisting of (e) to (f) below:
(e) a polynucleotide that hybridizes to a polynucleotide consisting of a nucleotide sequence complementary to the nucleotide sequence of SEQ ID NO: 1 under stringent conditions, and that encodes a protein having a lignan methylation activity; and,
(f) a polynucleotide that hybridizes to a polynucleotide consisting of a nucleotide sequence complementary to the nucleotide sequence of a polynucleotide encoding a protein consisting of the amino acid sequence of SEQ ID NO: 2 under stringent conditions, and that encodes a protein having a lignan methylation activity.

(2) The polynucleotide according to (1) above, which is selected from the group consisting of (g) and (h) below:
(g) a polynucleotide encoding a protein consisting of the amino acid sequence of SEQ ID NO: 2 or an amino acid sequence wherein 1 to 15 amino acids are deleted, substituted, inserted and/or added in the amino acid sequence of SEQ ID NO: 2, and having a lignan methylation activity; and, (h) a polynucleotide encoding a protein having an amino acid sequence having at least 80% identity to the amino acid sequence of SEQ ID NO: 2, and having a lignan methylation activity.

(2a) The polynucleotide according to (1) above which is shown below:

(i) a polynucleotide that hybridizes to a polynucleotide consisting of a nucleotide sequence of SEQ ID NO: 1 or a polynucleotide consisting of a nucleotide sequence complementary to the nucleotide sequence of SEQ ID NO: 1 under high stringent conditions, and that encodes a protein having a lignan methylation activity.

(3) The polynucleotide according to (1) above, comprising the nucleotide sequence of SEQ ID NO: 1.

(4) The polynucleotide according to (1) above, encoding a protein consisting of the amino acid sequence of SEQ ID NO: 2.

(5) The polynucleotide according to any one of (1) to (4) above, which is a DNA.

(6) A protein encoded by the polynucleotide according to any one of (1) to (5) above.

(7) A vector comprising the polynucleotide according to any one of (1) to (5) above.

(8) A non-human transformant introduced with the polynucleotide according to any one of (1) to (5) above.

(9) A non-human transformant introduced with the vector according to (7) above.

(10) A method for producing a protein having a lignan methylation activity, which comprises culturing or growing the transformant according to (8) or (9) above and collecting said protein from the transformant.

(11) The method according to (10) above, wherein the transformant is *Sesamum indicum*, *Forsythia intermedia* or *Linum usitatissimum* transformed by the polynucleotide according to any one of (1) to (5) above.

(12) A method for producing a methylated lignan which comprises culturing or growing the transformant according to (8) or (9) above and collecting the methylated lignan from the transformant.

(13) The method according to (12) above, wherein the transformant is *Sesamum indicum*, *Forsythia intermedia* or *Linum usitatissimum* transformed by the polynucleotide according to any one of (1) to (5) above.

Effects of the Invention

According to the present invention, lignans including thujaplicatin, etc. can be methylated and therefore, the present invention is useful in searching lignan compounds with new functions. Compounds searched using the gene of the invention or compounds obtained therefrom as intermediates may be used as active ingredients of drugs, functional food materials and molecules for new flower colors in horticultural plants. For example, methylthujaplicatin obtained in EXAMPLES later described is useful as an intermediate of podophyllotoxin known as an anticancer agent. Therefore, the present invention is useful in medical industries, food industries, agriculture, etc.

BEST MODES FOR CARRYING OUT THE INVENTION

As used herein, "lignans" are compounds in which two phenylpropanoid molecules having a $C_6C_3$ skeleton are dimerized mostly through the 8-8' position of these molecules (8,8'-linkage). Lignans are considered to contribute to biological defense mechanisms in plants (cf., Phytochemistry Rev. 2, 371-390 (2003)).

Representative lignans include (+)-sesamin, (+)-sesaminol, (+)-pinoresinol, (+)-piperitol and (+)-sesamolinol contained in *Sesamum indicum*; (+)-pinoresinol, (−)-arctigenin and (−)-matairesinol contained in *Forsythia intermedia*; (−)-pinoresinol and (−)-lariciresinol contained in *Daphne tangutica*; (+)-secoisolariciresinol contained in *Linum usitatissimum*; etc. Molecular structures of these lignans are diverse (cf., Wood Research 90, 27-110 (2003), etc.). (+)-Pinoresinol is a primary lignan and classified into furofuran lignans identified in the widest variety of plant species. Sesamin, which is one of the sesame lignans, displays an abundance of biological activities and is effective for improving cholesterol metabolism, liver function and immune function (see, e.g., Goma: SONO-KAGAKU-TO-KINOSEI (Sesame: Science and Function), edited by Mitsuo Namiki, Maruzen Planet Publishing Co. (1998)). Methods for the separation and purification of sesamin from sesame seeds or sesame lees have already been launched (c.f., e.g., Japanese Patent Laid-Open Publication (KOKAI) No. 2001-139579 and Japanese Patent Laid-Open Publication (KOKAI) No. 10-7676, etc.) and sesamin-based liver function improving/potentiating agents having an alcoholysis-promoting activity are commercially available (trade name: Sesamin, from sales agency Suntory, Ltd.). It is reported that lignans other than sesamin (c.f., e.g., sesaminol, sesamolin, etc.) also have biological activities (c.f., e.g., J. Bioscience, Biotechnology and Biochemistry, 76: 805-813 (2002)). As such, lignans or derivatives thereof are useful as physiologically active substances having various physiological activities or as intermediates thereof.

Hereinafter, the enzyme of the invention for transferring a methyl group to lignans, the polynucleotide encoding the enzyme, the vector comprising the polynucleotide, the transformant, etc. are described in detail.

1. Polynucleotide of the Invention

First, the present invention provides (a) a polynucleotide comprising the nucleotide sequence of SEQ ID NO: 1; and (b)

a polynucleotide encoding a protein consisting of the amino acid sequence of SEQ ID NO: 2. The polynucleotide may be a DNA or RNA.

The polynucleotides of the present invention are not limited to the polynucleotides (a) and (b) described above and further include other polynucleotides encoding proteins functionally equivalent to proteins encoded by these polynucleotides. The functionally equivalent proteins include, for example, (c) a protein consisting of an amino acid sequence wherein one or more amino acids are deleted, substituted, inserted and/or added in the amino acid sequence of SEQ ID NO: 2 and having the lignan methylation activity.

Such proteins include a protein consisting of an amino acid sequence wherein, e.g., 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2 or 1 amino acid(s) is/are deleted, substituted, inserted and/or added in the amino acid sequence of SEQ ID NO: 2, and having the lignan methylation activity. In general, the number of deletions, substitutions, insertions, and/or additions is preferably smaller. Furthermore, such proteins include a protein having an amino acid sequence having the identity of approximately 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, to (d) the amino acid sequence of SEQ ID NO: 2, and having the lignan methylation activity. In general, the higher the homology percentage described above is, the more preferred.

As used herein, the term "lignan methylation activity" is intended to mean an activity to methylate lignans, namely, an activity to transfer a methyl group to lignans. The "lignan methylation activity" can be assayed or confirmed by reacting methyl donor SAM and substrate lignan with lignan methyltransferase and analyzing the reaction product by HPLC or LC-MS. A general method for assaying the methyltransferase activity is described in known publications (cf., e.g., Toquin, V., et al. (2003) Plant Mol. Biol. 52, 495-509., Gang, D. R., et al. (2002) Plant Cell 14, 505-519, etc.).

The present invention further includes (e) a polynucleotide that hybridizes to a polynucleotide consisting of a nucleotide sequence complementary to the nucleotide sequence of SEQ ID NO: 1 under stringent conditions and encodes a protein having the lignan methylation activity; and (f) a polynucleotide that hybridizes to a polynucleotide consisting of a nucleotide sequence complementary to the nucleotide sequence of a polynucleotide encoding a protein consisting of the amino acid sequence of SEQ ID NO: 2 under stringent conditions and encodes a protein having the lignan methylation activity.

As used herein, the term "polynucleotide that hybridizes under stringent conditions" is intended to mean a polynucleotide (e.g., a DNA) obtained by the colony hybridization method, plaque hybridization method, Southern hybridization method or the like, using as a probe, for example, a polynucleotide consisting of a nucleotide sequence complementary to the nucleotide sequence of SEQ ID NO: 1, or the whole or part of a polynucleotide encoding the amino acid sequence of SEQ ID NO: 2. For hybridization, there are used methods described in, e.g., Molecular Cloning 3rd Ed., Current Protocols in Molecular Biology, John Wiley & Sons 1987-1997, etc.

As used herein, the "stringent conditions" may be any of low stringent conditions, moderate stringent conditions and high stringent conditions. The "low stringent conditions" are, for example, 5×SSC, 5×Denhardt's solution, 0.5% SDS and 50% formamide at 32° C. The "moderate stringent conditions" are, for example, 5×SSC, 5×Denhardt's solution, 0.5% SDS and 50% formamide at 42° C. The "high stringent conditions" are, for example, 5×SSC, 5×Denhardt's solution, 0.5% SDS and 50% formamide at 50° C. Under these conditions, a polynucleotide (e.g., a DNA) with higher homology is expected to be obtained efficiently at higher temperatures. However, multiple factors are involved in hybridization stringency including temperature, probe concentration, probe length, ionic strength, time, salt concentration and others, and those skilled in the art may appropriately choose these factors to achieve similar stringency.

When commercially available kits are used for hybridization, for example, Alkphos Direct Labeling Reagents (manufactured by Amersham Pharmacia Inc.) may be used. In this case, according to the protocol attached to the kit, cultivation is performed with a labeled probe overnight and the membrane is washed with a primary wash buffer containing 0.1% (w/v) SDS under conditions at 55° C.; then the hybridized polynucleotide (e.g., DNA) can be detected.

In addition to those described above, other polynucleotides that can be hybridized include DNAs having the identity of approximately 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher, with the polynucleotide encoding the amino acid sequence of SEQ ID NO: 2, as calculated by a homology search software, such as FASTA, BLAST, etc. using default parameters.

Identity between amino acid sequences or nucleotide sequences may be determined using algorithm BLAST by Karlin and Altschul (Proc. Natl. Acad. Sci. USA 872264-2268, 1990; Proc. Natl. Acad. Sci. USA 90: 5873, 1993). Programs called BLASTN and BLASTX based on the BLAST algorithm have been developed (Altschul S F, et al: J. Mol. Biol. 215: 403, 1990). When a nucleotide sequence is sequenced using BLASTN, the parameters are, for example, score=100 and wordlength=12. When an amino acid sequence is sequenced using BLASTX, the parameters are, for example, score=50 and wordlength=3. When BLAST and Gapped BLAST programs are used, default parameters for each of the programs are employed.

The polynucleotides of the present invention described above can be obtained by known genetic engineering techniques or known synthesis methods.

2. Protein of the Invention

The present invention also provides a protein encoded by any one of the polynucleotides (a) to (i) described above. The proteins which are preferred in the present invention are proteins consisting of an amino acid sequence in which one or more amino acids are deleted, substituted, inserted and/or added in the amino acid sequence of SEQ ID NO: 2, and having the lignan methylation activity.

Such proteins include a protein consisting of an amino acid sequence wherein amino acid residues with the number described above are deleted, substituted, inserted and/or added in the amino acid sequence of SEQ ID NO: 2, and having the lignan methylation activity. Such proteins also include a protein having an amino acid sequence having the homology described above to the amino acid sequence of SEQ ID NO: 2, and having the lignan methylation activity.

These proteins may be obtained by using site-directed mutagenesis described in, e.g., "Molecular Cloning, 3rd edition," "Current Protocols in Molecular Biology," "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", "Proc. Natl. Acad. Sci. USA, 82, 488 (1985)," etc.

The deletion, substitution, insertion and/or addition of one or more amino acid residues in the amino acid sequence of the protein of the invention is/are intended to mean that one or more amino acid residues are deleted, substituted, inserted and/or added at one or more positions in the same amino acid sequence. Two or more types of deletions, substitutions, insertions and additions may occur at the same time.

Examples of the amino acid residues which are mutually substitutable are given below. Amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may also be produced by chemical synthesis methods such as the Fmoc method (fluorenylmethyloxycarbonyl method), the tBoc method (t-butyloxycarbonyl method), etc. In addition, peptide synthesizers available from Advanced ChemTech, Inc., PerkinElmer, Inc., Pharmacia, Protein Technology Instrument, Synthecell Vega Corp., PerSeptive, SHIMADZU Corp., etc. may also be used for the chemical synthesis.

The protein of the present invention can catalyze the methylation of lignans (especially, thujaplicatin) described above.

3. Vector and Transformant Introduced with the Vector

Next, the present invention provides the vector comprising the polynucleotide described above. The vector of the present invention comprises the polynucleotide (DNA) defined in any one of (a) to (i) described above.

In general, the vector of the invention is constructed to contain an expression cassette comprising (i) a promoter that can be transcribed in a host cell; (ii) the polynucleotide described in any one of (a) to (j) above that is linked to the promoter; and (iii) a signal that functions in the host cell with respect to the transcription termination and polyadenylation of RNA molecule. The vector thus constructed is introduced into a host cell. The expression vector may be prepared according to a method using a plasmid, phage, cosmid, etc., but the method is not particularly limited thereto.

The vector is not particularly limited to specific types and vectors that can be expressed in host cells may be appropriately chosen. In other words, a promoter sequence is appropriately chosen to ensure the expression of the polynucleotide of the present invention depending upon type of host cells; this one and the polynucleotide of the present invention may be incorporated into various plasmids, etc., and the vectors thus obtained may be used as expression vectors.

The expression vector of the present invention contains expression regulatory regions (e.g., a promoter, terminator and/or replication origin, etc.) depending upon type of the host to be introduced. As the promoter for bacteria, there are employed conventional promoters (e.g., a trc promoter, tac promoter, lac promoter, etc.). As the promoter for yeast, a glyceraldehyde 3-phosphate dehydrogenase promoter, PHO5 promoter, etc. may be used. The promoter for filamentous fungi includes, for example, promoters of amylase, trpC, etc. The promoter for animal cell hosts includes viral promoters (e.g., SV40 early promoter, SV40 late promoter, etc.).

Preferably, the expression vector contains at least one selection marker. The marker available includes an auxotrophic marker (ura5, niaD), a drug-resistant marker (hygromycin, zeocin), a geneticin-resistant marker (G418r), a copper-resistant gene (CUP1) (Marin et al., Proc. Natl. Acad. Sci. USA, 81, 337, 1984), a cerulenin-resistant gene (fas2m, PDR4) (Junji Inokoshi et al., Biochemistry, 64, 660, 1992; and Hussain et al., Gene, 101: 149, 1991, respectively), etc.

The present invention further provides the transformant introduced with the polynucleotide according to any one of (a) to (i) described above.

4. Transformant

The present invention provides the transformant or cell in which the polynucleotide encoding the protein having the lignan methylation activity described above is introduced. As used herein, the term "transformant" is intended to mean not only a tissue or organ but also an individual organism.

Methods for preparing (producing) the transformants or cells are not particularly limited, and include, for example, the aforesaid method which involves transformation through incorporation of a recombinant vector into a host. The host cells used herein are not particularly limited and various cells heretofore known may be advantageously used. Specific examples include, but not limited to, bacteria such as *Escherichia coli*, etc., yeast (*Saccharomyces cerevisiae* and *Schizosaccharomyces pombe*), *Caenorhabditis elegans* or oocytes of *Xenopus laevis*, etc. Media for incubation and conditions suitable for the host cells described above are well known in the art. Organisms to be transformed are not particularly limited, and examples include various microorganisms, plants or animals illustratively given for the host cells described above.

The transformants or cells of the present invention are characterized in that their compositions are changed from those of naturally occurring lignans and/or methylated lignans. The transformants or cells of the present invention are preferably plants or their progeny, or tissues derived therefrom, more preferably, *Sesamum indicum, Forsythia intermedia* or *Linum usitatissimum*. In these transformants or cells, the content of methylated lignans in organisms capable of producing lignans can be increased or decreased by the method of controlling the contents of methylated lignans of the present invention.

The transformant of the present invention may be a plant transformant. The plant transformant in this embodiment can be acquired by introducing a recombinant vector comprising the polynucleotide of the present invention into a plant in such a manner that the protein encoded by the polynucleotide can be expressed.

Where a recombinant expression vector is used, the recombinant expression vector used to transform the plant is not particularly limited as far as the vector is capable of expressing the polynucleotide of the present invention in said plant. Examples of such vectors include a vector bearing a promoter capable of constitutively expressing the polynucleotide in plant cells (e.g., a 35S promoter of cauliflower mosaic virus) in plant cells, and a vector inducibly activated by external stimulation.

Plants that are subject to transformation in the present invention are intended to mean entire plant bodies, plant organs (e.g., leaves, petals, stems, roots, seeds, etc.), plant tissues (e.g., epidermis, phloem, parenchyma, xylem, vascular bundles, palisade tissues, spongy tissues, etc.) or plant culture cells, or any of various types of plant cells (e.g., suspension culture cells), protoplasts, leaf slices, calluses, and the like. Plant species which are used for transformation are not limited but may be any plant from those belonging to the Monocotyledoneae or the Dicotyledoneae.

Conventional transformation methods (e.g., the *Agrobacterium* method, gene gun, the PEG method, the electroporation method, etc.) known to one skilled in the art are used to transform genes to plants. For example, the *Agrobacterium*-mediated method and the method of directly introducing into plant cells are well known. When the *Agrobacterium* method is used, the plant expression vector constructed is introduced into an appropriate *Agrobacterium* strain (e.g., *Agrobacterium tumefaciens*), followed by infection of aseptically cultured leaf discs with this strain according to the leaf disc method (Hirobumi Uchimiya, Manuals for Plant Gene Manipulation (1990), 27-31, Kodansha Scientific Co., Ltd., Tokyo), etc. The transgenic plant can thus be obtained. The method of Nagel, et al. (Microbiol. Lett., 67, 325 (1990)) may also be used. This method involves introducing first, e.g., an expression vector into *Agrobacterium* and then introducing the transformed *Agrobacterium* into plant cells or plant tissues by the method described in Plant Molecular Biology Manual (S. B. Gelvin, et. al., Academic Press Publishers). Herein, the "plant tissue" includes callus obtained by culturing plant cells. When the transformation is carried out using the *Agrobacterium* method, binary vectors (pBI121 or pPZP202, etc.) may be used.

For direct transfer of genes to plant cells or plant tissues, the electroporation method and the gene gun method are known. When a gene gun is used, entire plant bodies, plant organs or plant tissues per se may be used, or protoplasts may be prepared and then provided for use. The samples thus prepared can be bombarded using a gene transfer apparatus (e.g., PDS-1000 (BIO-RAD, Inc.), etc.). Bombardment conditions may vary depending upon type of plants or samples. Normally, the bombardment is performed under a pressure of about 450-2000 psi at a distance of 4-12 cm.

The cells or plant tissues into which the gene is introduced are first selected for their chemical resistance such as hygromycin resistance, etc. and then regenerated into plant bodies in a conventional manner. Regeneration of plant bodies from the transformant cells can be performed by methods known to one skilled in the art, depending upon kind of plant cells. Where a plant culture cell is used as a host, transformation is preformed by introducing the recombinant vector into culture cells by the gene gun method, the electroporation method, etc. Calluses, shoots, hairy roots, etc. resulted from the transformation can be used directly in cell culture, tissue culture or organ culture. Furthermore, they can be regenerated into plant bodies by conventional plant tissue culture methods through administration of plant hormones (e.g., auxin, cytokinin, gibberellin, abscisic acid, ethylene, brassinolide, etc.) at appropriate concentrations.

Whether the gene is introduced into the host or not can be confirmed by PCR, Southern hybridization, northern hybridization, or the like. For example, a DNA is prepared from the transgenic plant and DNA-specific primers are designed to perform PCR.

Once the transgenic plant wherein the polynucleotide of the present invention is incorporated into the genome is acquired, its progeny can be obtained by sexual or asexual reproduction of the plant body. Also, the plant body can be mass-produced by acquiring from the plant body or its progeny or clones thereof; e.g., seeds, fruits, cut panicles, tubers, tuberous roots, strains, calluses, protoplasts, etc., and then using them as the origin. Accordingly, the present invention also encompasses the plant body wherein the polynucleotide of the present invention is expressibly introduced, or progenies of the plant body having the same property as in the plant body, and tissues derived therefrom.

The transformation methods for various plants are already reported. Examples of the transgenic plants of the invention include, but are not limited to, sesame, rice plant, tobacco, barley, wheat, rapeseed, potato, tomato, poplar, banana, eucalyptus, sweet potato, soybean, alfalfa, lupinus, corn, cauliflower, rose, chrysanthemum, carnation, snapdragon, cyclamen, orchid, Prairie gentian, freesia, gerbera, gladiolus, gypsophila, kalancoe, lily, pelargonium, geranium, petunia, torenia, tulip, *Forsythia intermedia, Arabidopsis thaliana, Linum usitatissimum, Anthrissus sylvestris, Lotus japonicus*, and so on.

In a preferred embodiment, the transformant of the present invention can be prepared using sesame. The method of preparing the transgenic sesame includes such a known method as described in, for example, T. Asamizu: Transformation of sesame plants using MAT vector system: introduction of fatty acid desaturase genes, Sesame Newsletter, 16: 22-25 (2002).

By using the transgenic sesame thus obtained, the methylated lignans are produced in the sesame. Thus, the methylated lignans (e.g., methylthujaplicatin) can be produced at low costs by an environment-friendly production process.

In another preferred embodiment, a tobacco plant can be used preferably as the transformant of the present invention. In addition to petunia, the tobacco plant is a typical plant which readily undergoes transformation and is capable of regenerating from a cell wall-removed single cell (protoplast) to a single plant body. This single plant body regenerated does not result in a chimeric pattern unlike the single body derived from multiple cells so that its transformants can be efficiently produced.

A preferred example of the transformation method for tobacco is the leaf disc method. According to this method, operations are easy and multiple independent transformants can be obtained from a single leaf disc. The transformation method is described in, e.g., "SHIN-SEIBUTSU KAGAKU JIKKEN-NO-TEBIKI (New Guidance of Biochemical Experiment) 3: Isolation/Analysis of Nucleic Acid and Gene Research Method, published by Kagaku Dojin, 1996."

By using the transgenic tobacco thus obtained, the lignan methyltransferase can be produced at low costs by an environment-friendly production process.

In yet another preferred embodiment, a rice plant can be advantageously employed as the transformant of the present invention. By using the transgenic rice plant, the lignan methyltransferase can be produced in the rice plant at low costs by an environment-friendly production process.

Where organisms contain lignans (especially thujaplicatin), irrespective of species of organisms, the transformant of the present invention can produce the methylated lignans by introducing the aforesaid polynucleotide therein.

When the transformant introduced with a recombinant expression vector comprising the polynucleotide encoding the protein of the present invention is used, the transformant can catalyze the reaction to methylate endogenous lignans present in organisms such as plants. Thus, the methylated lignans can be mass-produced at low costs by an environment-friendly production process. Furthermore, the present invention can provide inexpensive foodstuff or industry products by mass-producing methylated lignans.

By using the transformant of the present invention, the protein that catalyzes the lignan methylation can be provided at low costs under environment-friendly conditions.

In an embodiment, the cells in accordance with the present invention may be a variety of bacterial hosts. The cells in accordance with the embodiment are obtained by introducing a recombinant vector comprising the polynucleotide of the present invention into cells in such a manner that the protein encoded by the polynucleotide can be expressed.

According to the disclosure in the specification, one skilled in the art can easily understand that the lignan methylation ability can be imparted to organisms over a wide range from bacteria to higher plants, once a recombinant expression vector comprising the polynucleotide encoding the protein having the lignan methylation activity is introduced.

Where an organism contains lignans (especially thujaplicatin), irrespective of the species of organism, the cells of the present invention can produce the methylated lignans by introducing the aforesaid polynucleotide.

When the cells wherein a recombinant expression vector comprising the polynucleotide encoding the protein of the present invention is used, the lignan methylation reaction can be catalyzed within the cells. Thus, the methylated lignans can be mass-produced at low costs by an environment-friendly production process. In addition, the present invention can provide inexpensive foodstuffs or industry products through the mass-production of methylated lignans.

By using the cells in accordance with the present invention, the protein that catalyzes the lignan methylation reaction can be provided at low costs under environment-friendly conditions.

5. Method for Producing Protein of the Invention

In another embodiment, the present invention provides the method for producing the protein of the present invention. Specifically, the protein of the present invention can be obtained by isolating and purifying the protein of the invention from the culture product of the transformant described above. As used herein, the culture product means any of a culture solution, a cultured microorganism or cultured cell, or a cultured cell lysate. The protein of the present invention can be isolated and purified in a conventional manner.

Where the protein of the invention is accumulated in, e.g., cultured microorganisms or cells, the microorganisms or cells are lysed, after incubation, in a conventional manner (e.g., ultrasonication, lysozyme, freezing and thawing, etc.) and then treated in a conventional manner (e.g., centrifugation, filtration, etc.) to give the crude extract of the protein of the invention. Where the protein of the invention is accumulated in a culture solution, the microorganisms or cells are separated from the culture supernatant, after completion of the culture, in a conventional manner (e.g., centrifugation, filtration, etc.). Thus, the culture supernatant containing the protein of the invention can be obtained.

The protein of the present invention contained in the extract or culture supernatant thus obtained can be purified in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination thereof 6. Method for Producing Methylated Lignan The present invention provides the method for producing methylated lignans using organisms or cells expressing the protein of the present invention. The organisms described above may be naturally occurring intact organisms or transgenic organisms produced using the recombinant expression system. According to the method for producing methylated lignans, lignans (especially, thujaplicatin) can be produced efficiently.

In an embodiment, the method for producing methylated lignans of the present invention comprises producing the methylated lignans using the organism transformed with the polynucleotide encoding the protein of the present invention or its tissues. Preferably, the organisms described above include the transgenic plants or cells described above, especially preferably, *Escherichia coli, Sesamum indicum, Forsythia intermedia* or *Linum usitatissimum*.

The method for producing methylated lignans of the present invention comprises the step of introducing the polynucleotide encoding the protein of the present invention into the organism described above. For the step of introducing the polynucleotide into the organism described above, the various gene transfer methods described above may be used. In this aspect of the embodiment, the organism described above has different compositions between the methylated lignans produced before transformation and those produced after transformation. Specifically, the lignans and methylated lignans obtained from the organism described above provide an increased content of the lignans and methylated lignans. The method for producing the methylated lignans from this aspect of the embodiment further comprises the step of extracting the methylated lignans from the organism described above.

7. Foodstuff and Industrial Product

The present invention provides foodstuffs and industrial products using methylated lignans, which are obtained by the method for producing the methylated lignans described above. The foodstuffs referred to in this section may be any of seeds, fruits, cut panicles, tubers and/or tuberous roots, etc. of the transgenic plants described above, or ma be foodstuffs (e.g., Sesamum indicum, Forsythia intermedia or Linum usitatissimum, or processed foodstuffs thereof) manufactured using the methylated lignans extracted from the transgenic plants described above. The foodstuffs or industrial products of the present invention may contain a desired amount of lignans (especially, thujaplicatin).

For example, the solutions obtained by extracting methylated lignans from the transgenic plants of the present invention, in which the content of methylated lignans is increased as described above, can be provided as methylated lignan-rich foodstuffs. In addition to the methylated lignans extracted, the seeds, fruits, cut panicles, tubers and/or tuberous roots, etc. of the transgenic plants described above can also be provided as methylated lignan-rich foodstuffs. The target for alteration of the methylated lignan composition is not particularly limited but all organisms including animals, bacteria, yeast, etc. may be targeted, in addition to plants.

Based on unique physical properties of lignans and methylated lignans, the proteins or polynucleotides of the present invention can be used as raw materials for industrial products (e.g., industrial products such as films, biodegradable plastics, functional fibers, lubricants or detergents).

The present invention will be described in more detail by referring to the following EXAMPLES but is not deemed to be limited thereto.

EXAMPLES

Example 1

Gene Cloning

Molecular biological strategies used in this EXAMPLE were implemented by the method described in Molecular Cloning (Sambrook et al., Cold Spring Harbour Laboratory Press, 2001), unless otherwise specified in detail.

Total RNA was extracted from young leaves and roots of Anthrissus sylvestris using a RNeasy Plant Mini Kit (QIAGEN) and subsequently purified using an Oligotex-dT mRNA Purification Kit (TaKaRa Bio) to give PolyA(+)RNA. Using 4 µg of this PolyA(+)RNA, a cDNA library was constructed using a Lambda ZAPII Directional cDNA Library Synthesis Kit (Stratagene Corp.) in accordance with the protocol recommended by the manufacturer.

Using approximately 300,000 pfu of phage containing the cDNA library described above, screening was performed by plaque hybridization, using as a screening probe a mixture of fragments amplified with the four OMT-gene specific primer sets described in TABLE 1. The probes were labeled by PCR using a Non-Radioisotope DIG-Nucleic Acid Detection System (Roche Diagnostics K.K.) under the conditions recommended by the manufacturer. In this case, the cDNA from *Carthamus tinctorius* was used as a template with respect to the OMT primer sets 1 and 2 (Set 1 Forward: SEQ ID NO: 3; Set 1 Reverse: SEQ ID NO: 4; Set 2 Forward: SEQ ID NO: 5; Set 2 Reverse: SEQ ID NO: 6). With respect to the OMT primer sets 3 and 4, the cDNA from *Populus alba* was used as a template (Set 3 Forward: SEQ ID NO: 7; Set 3 Reverse: SEQ ID NO: 8; Set 4 Forward: SEQ ID NO: 9; Set 4 Reverse: SEQ ID NO: 10). The reaction solution containing 1 µl of the template cDNA, 1× Taq buffer (TaKaRa Bio), 0.2 mM dNTPs, 0.2 pmol/µl each of the gene-specific primers shown in TABLE 1 and 1.25 U rTaq polymerase was used. PCR of this solution was carried out at 94° C. for 5 minutes, and then in 30 cycles at 94° C. for 1 minute, at 52° C. for 1 minute and at 72° C. for 2 minutes. Finally, the product was treated at 72° C. for 5 minutes. The primers and unreacted dNTPs were removed from the PCR product using a Mini Quick Spin Column (Roche), and the product was used as a probe.

Screening of libraries and detection of positive clones were performed using a Non-Radioisotope DIG-Nucleic Acid Detection System (Roche Diagnostics) according to the protocol recommended by the manufacturer. Hybridization was performed in 5×SSC containing 30% formamide at 37° C. overnight, and the membrane was washed in 4×SSC using 1% SDS at 55° C. for 20 minutes. Approximately 400,000 plaques were screened, and cDNA sequence was obtained from the resulting positive clones by primer walking with synthetic oligonucleotide primers using a DNA Sequencer Model 3100 (Applied Biosystems). The cDNA sequence obtained was subjected to homology search with the Blastx program (http://blast.ncbi.nlm.nih.gov/Blast.cgi) to give Anthrissus sylvestris methyltransferase-like gene (AsOMT).

AsOMT clone 116 (hereinafter AsOMT116) represented by SEQ ID NO: 1 and SEQ ID NO: 2 showed low homology (ca. 51%) with *Rosa chinensis* phloroglucinol O-methyltransferase (Accession No. BAD18975) by the Blastx program, but any clear function could not be predicted. Therefore, the clone was expressed in *Escherichia coli*, which was provided for function analysis. cDNA Sequence of AsOMT116 (SEQ ID NO: 1)

ATGTCTAAACAAGATCAAGATGCCACTGAATTCACAAGGGTGCTGCAGG

TAAGTGGTGGCATAATTCTTGGAATGGTATTGAAAGCTGCTGTTGAGTT

TAATCTTTTCGAGATCATGGCCAATGCTGCTGCTGTTGATGGAGCTTCT

CCTTTCGGAGATGATGCTAAGAAGTTGTCTAGTGATGATATTGTAGCTC

ATCTTCCCACACAAAATCCTGCAGCTACTGCAATGCTGGAGCGAATTCT

TCGGTTTCTGTCTGCTCATTCCTTTCTTACCAGGACCGTAGTAGCTGGA

GAAGGTGGCCAGGAACAGAGTTTGTATGGTCTAGAAAGTATTTGCAAGA

ATTACATTCCTGATCAAGATGGTGTTTCATTTGCTCCTTTATTGGTTAT

GCTTCATGACAAAGTTATCATCGATTCTTTGTTGTGCTTGAAAGATGCA

CTTCTTGAGGGAGGTATTCCGTTTAACAAGGCTCATGATGGCATGGATG

CATTTGAATACCCTGCAATAGACAGCAGATTCAATGACGTTTTCAATCA

AGCAATGTACAACCACACCACTTTAATCATGAAGAAGATTCTAGAAGTT

TACGCTGGATTCGAAGAACTCACAGAGATTGTAGATGTTGGTGGTGGAA

CCGGGGCAACACTAGCCAAAATCATGTCCAAATATCCTCATATCAGGGG

AATCAACTTCGATTTGCCTCATGTCATCAAGAACGCCCCTCCTTTAGCT

GGTGTGGAGCATGTGGGAGGAGATATGTTTGAAAGTGTCCCGAAAGGAG

AGGTCATCTTCATGAAGTGGATACTTCATGATTGGAGCGATGGACACTG

CTTAAAGCTTTTGCAGAATTGCTGCAACTCCCTTCCAGAATCTGGCAAG

GTGATAATTGTAGAATCAATAGTGCCAGAGAATACGAACACAGGTTCTT

TABLE 1

| OMT primer | Forward | Reverse |
|---|---|---|
| Set1 | 5'-ggaactctggttgatgttggtg-3' | 5'-cgatgatggattcaattgcagga-3' |
| Set2 | 5'-tgaagaccttggtggatgttgg-3' | 5'-tatgaaatcctttgaagccggcag-3' |
| Set3 | 5'-tgaaggcctcacgtccttggt-3' | 5'-tggaagccagctcccttagct-3' |
| Set4 | 5'-cgccagaattgtgatgaaggct-3' | 5'-gtaacgactaaacccgccttcca-3' |

-continued

CATCGGAATTAAGCAATGTCATGAGCAATGATATGGTAATGCTGGCAGT

AAATCCGGAGGAAAGGAGAGGAGTATCAAAGAATTTGAGGCATTGGCA

AAAGAATCTGGATTCGCCACCGTAGAACTCATATGCAGCGTCGCTATAT

ATAGTGTTCTAGAATTTCATAAGAAAGTG

Amino acid sequence of AsOMT116 (SEQ ID NO: 2) in one letter code

MSKQDQDATEFTRVLQVSGGIILGMVLKAAVEFNLFEIMANAAAVDGAS

PFGDDAKKLSSDDIVAHLPTQNPAATAMLERILRFLSAHSFLTRTVVAG

EGGQEQSLYGLESICKNYIPDQDGVSFAPLLVMLHDKVIIDSLLCLKDA

LLEGGIPFNKAHDGMDAFEYPAIDSRFNDVFNQAMYNHTTLIMKKILEV

YAGFEELTEIVDVGGGTGATLAKIMSKYPHIRGINFDLPHVIKNAPPLA

GVEHVGGDMFESVPKGEVIFMKWILHDWSDGHCLKLLQNCCNSLPESGK

VIIVESIVPENTNTGSSSELSNVMSNDMVMLAVNPGGKERSIKEFEALA

KESGFATVELICSVAIYSVLEFHKKV

Example 2

Construction of Expression Vector

A full length ORF of AsOMT116 was amplified by RT-PCR using the restriction enzyme site-added primers (TABLE 2: uppermost row: SEQ ID NO: 11; lowermost row: SEQ ID NO: 12).

TABLE 2

Primers for Subcloning

| Primer name | Sequence |
|---|---|
| AsOMTExp-116-F #481 | 5'-GGAATTCGCTAGCATGTCTAAACAAGATC-3' |
| AsOMTExp-116-R #482 | 5'-ATTTCTCGAGCACTTTCTTATGAAATTCTA-3' |

The Anthrissus sylvestris cDNA was obtained by reverse transcription using as a template 1 μg of total RNA from Anthrissus sylvestris. The cDNA was synthesized on Super-Script™ First-Strand Synthesis System for RT-PCR (GIBCO BRL) under the synthesis conditions recommended by the manufacturer.

The PCR solution (50 μA contained 1 μl of the Anthrissus sylvestris cDNA, 1× ExTaq buffer (TaKaRa Bio), 0.2 mM dNTP, 0.4 pmol/μl each of the primers (TABLE 3) and 2.5 U ExTaq polymerase. This PCR solution was reacted at 94° C. for 3 minutes, and then in 30 cycles at 94° C. for 1 minute, at 50° C. for 1 minute and at 72° C. for 2 minutes. The PCR product was electrophoresed on 1% agarose gel and then stained with ethidium bromide. The results confirmed that the amplification product of approximately 1.1 kb size deduced from the full length ORF of AsOMT116 was obtained.

This PCR product was subcloned onto pBluescript SK+Vector (Stratagene). It was confirmed by primer walking using a DNA Sequencer Model 3100 (Applied Biosystems) that any mutation by PCR did not occur in the inserted fragment.

The AsOMT116 fragment of approximately 1.1 kb was excised using the restriction enzyme sites of NheI and XhoI added to the primers. This fragment was ligated to the NheI and XhoI site of Escherichia coli expression vector pET23a (Novagen Inc.) to give Escherichia coli expression vector of this enzyme gene. It was designed to express a chimeric protein of AsOMT116 having His tag downstream of the XhoI site of this vector and the open reading frame of the AsOMT116 gene and the His tag.

Example 3

Analysis of Enzyme Function

To clarify the biochemical enzyme functions, the enzymes were expressed in Escherichia coli. Using the plasmid for expression of AsOMT116 Escherichia coli obtained above, Escherichia coli BL21 (DE3) strain was transformed in a conventional manner. The resulting transformants were inoculated in 4 ml of LB medium (10 g/l tryptone peptone, 5 g/l yeast extract, 1 g/l NaCl) containing 50 μg/ml of ampicillin followed by shake culture at 37° C. overnight. When the cells reached the stationary phase, 4 ml of the culture broth was inoculated into 80 ml of fresh medium of the same composition, followed by shake culture at 37° C. At the point when the cell turbidity (OD600) reached approximately 0.5, 0.5 mM IPTG in a final concentration was added to the cells, followed by shake culture at 18° C. for 20 hours.

The following procedures were all carried out at 4° C. The transformants cultured were collected by centrifugation (5,000×g, 10 minutes) and suspended by adding 1 ml/g cell of lysis buffer (20 mM HEPES buffer (pH 7.5), 14 mM β-mercaptoethanol). Subsequently, the suspension was ultrasonicated (15 secs.×8 times) and then centrifuged (15,000×g, 15 minutes). The supernatant (soluble fraction) obtained was recovered as a crude enzyme solution. The crude enzyme solution was used for enzyme analysis.

Conditions for the enzyme reaction are as follows. The reaction solution (0.04 mM S-adenosylmethionine, 50 mM Tris-HCl buffer (pH 7.5), 2 mM $MgCl_2$, 0.01 mM substrate (thujaplicatin) and about 3 mg of the crude enzyme) was prepared into a 50 μl solution, which was reacted at 30° C. for an hour.

The enzyme reaction solution was extracted with ethyl acetate. The extract was dried and dissolved in 10 μl of N,O-bis(trimethylsilyl)acetamide for trimethylsilylation (TMS), followed by GC-MS analysis under the following conditions.

Analytical instrument: SHIMADZU GCMS-QP2010 Plus Mass Spectrometer System
Mode: electron impact
Column: 10 m Shimadzu CPB 10-M25
Carrier gas: helium
Injection temperature: 250° C.
Column temperature: 160° C. to 250° C., speed, 20° C./min.

Figure 1:
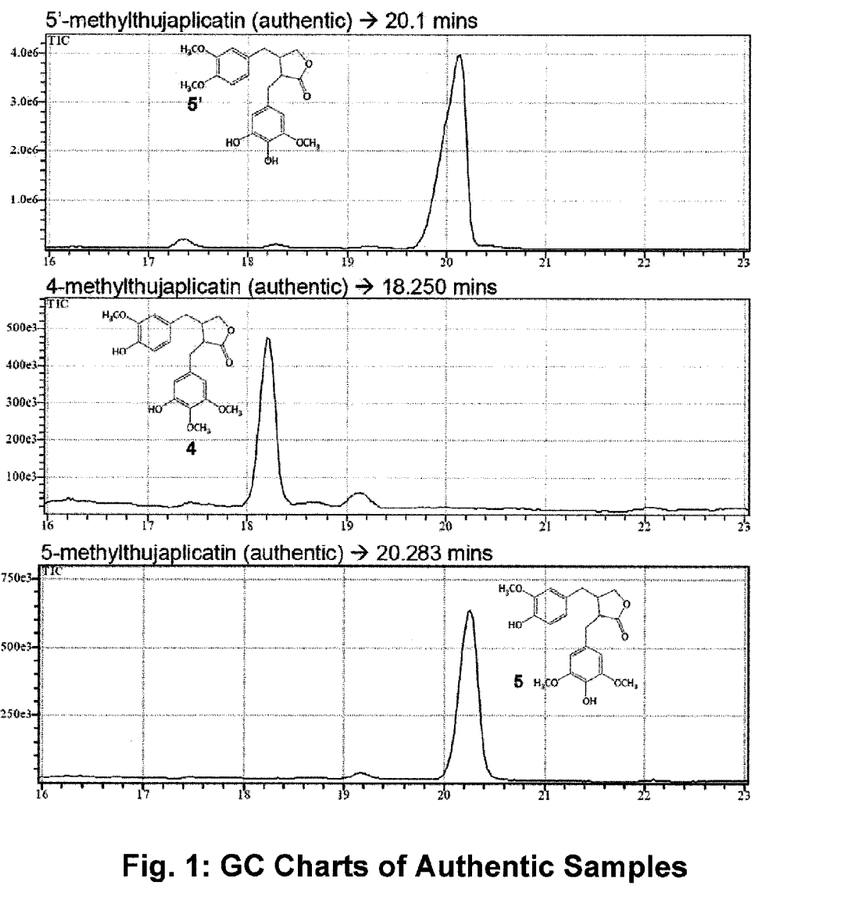
FIG. 1 shows GC-MS charts using authentic samples of 5'-methylthujaplicatin (uppermost row), 4-methylthujaplicatin (middle row) and 5-methylthujaplicatin (lowermost row), respectively. TIC stands for Total Ion Chromatogram.
Figure 2:
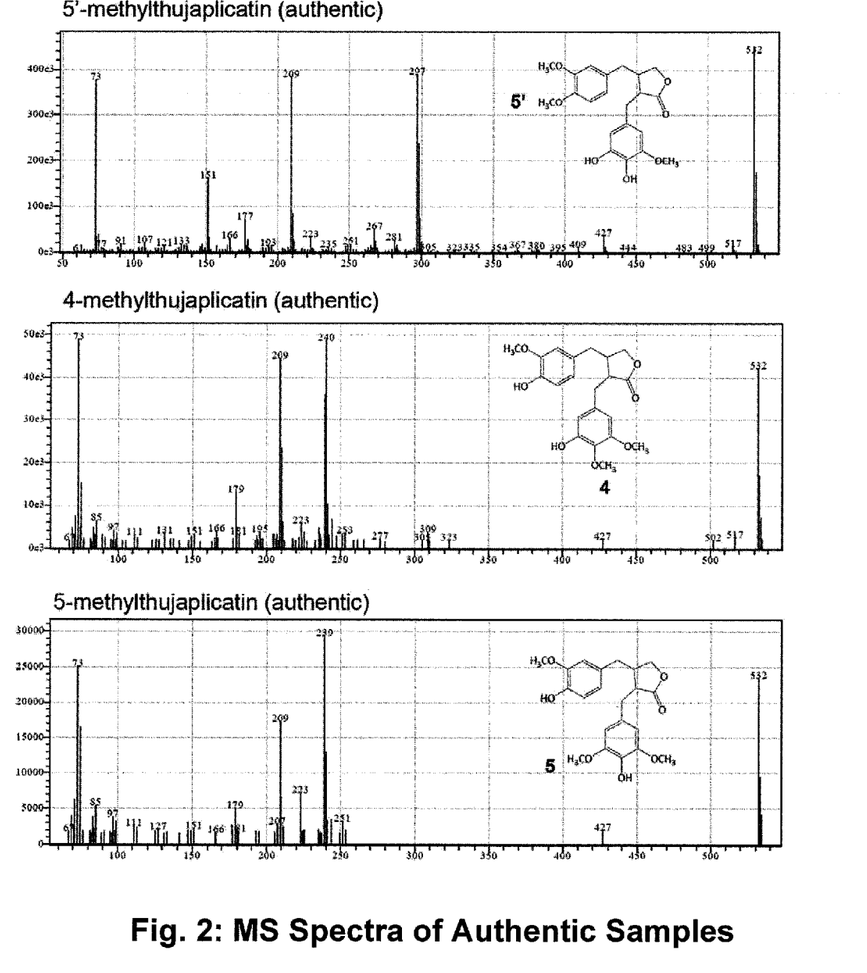
FIG. 2 shows MS spectra using authentic samples of 5'-methylthujaplicatin (uppermost row), 4-methylthujaplicatin (middle row) and 5-methylthujaplicatin (lowermost row), respectively. The ions at 532 commonly observed in the respective samples indicate TMS methylthujaplicatin.
Figure 3:
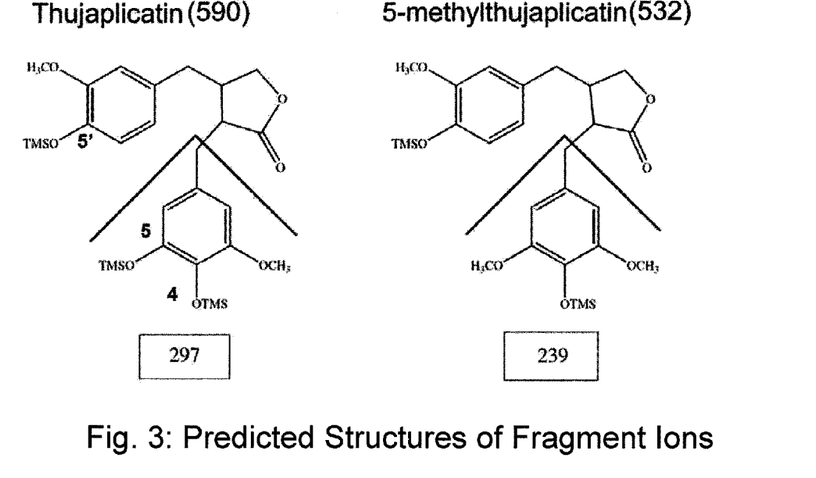
FIG. 3 shows enzymatic reaction substrates thujaplicatin (formula on the left) and 5-methylthujaplicatin (formula on the right). The numerical values in the figure indicate predicted MS spectrum values of the fragment ions formed when the respective chemical formulas were cleaved at the positions shown by bold polygonal lines.

The authentic samples were prepared according to the prior publication supra (Sakakibara, N., et al (2003) Org. Biomol. Chem. 1, 2474-2485) and provided for use. Under the conditions, authentic 5'-methylthujaplicatin, 5-methylthujaplicatin and 4-methylthujaplicatin were eluted at approximately 20.1 minutes, 20.3 minutes and 18.3 minutes, respectively (FIG. 1). It was confirmed that 5'-methylthujaplicatin and 5-methylthujaplicatin were similar in retention time but could be distinguished from each other by their MS fragment patterns (FIG. 2). For example, the fragment ion at 239 observed with 5-methylthujaplicatin was not observed with 5'-methylthujaplicatin; conversely, the fragment ion at 297 observed with 5'-methylthujaplicatin was not observed with 5-methylthujaplicatin (FIG. 2). In all monomethylated thujaplicatins, the parent ion for TMS-thujaplicatin (where the hydroxy group is trimethylsilylated) at 532 was observed. Based on the fragment ion at 239 observed with the 5-methylthujaplicatin and the fragment ion at 297 observed with the 5'-thujaplicatin, the structures were predicted for these thujaplicatins (FIG. 3).

Figure 4:
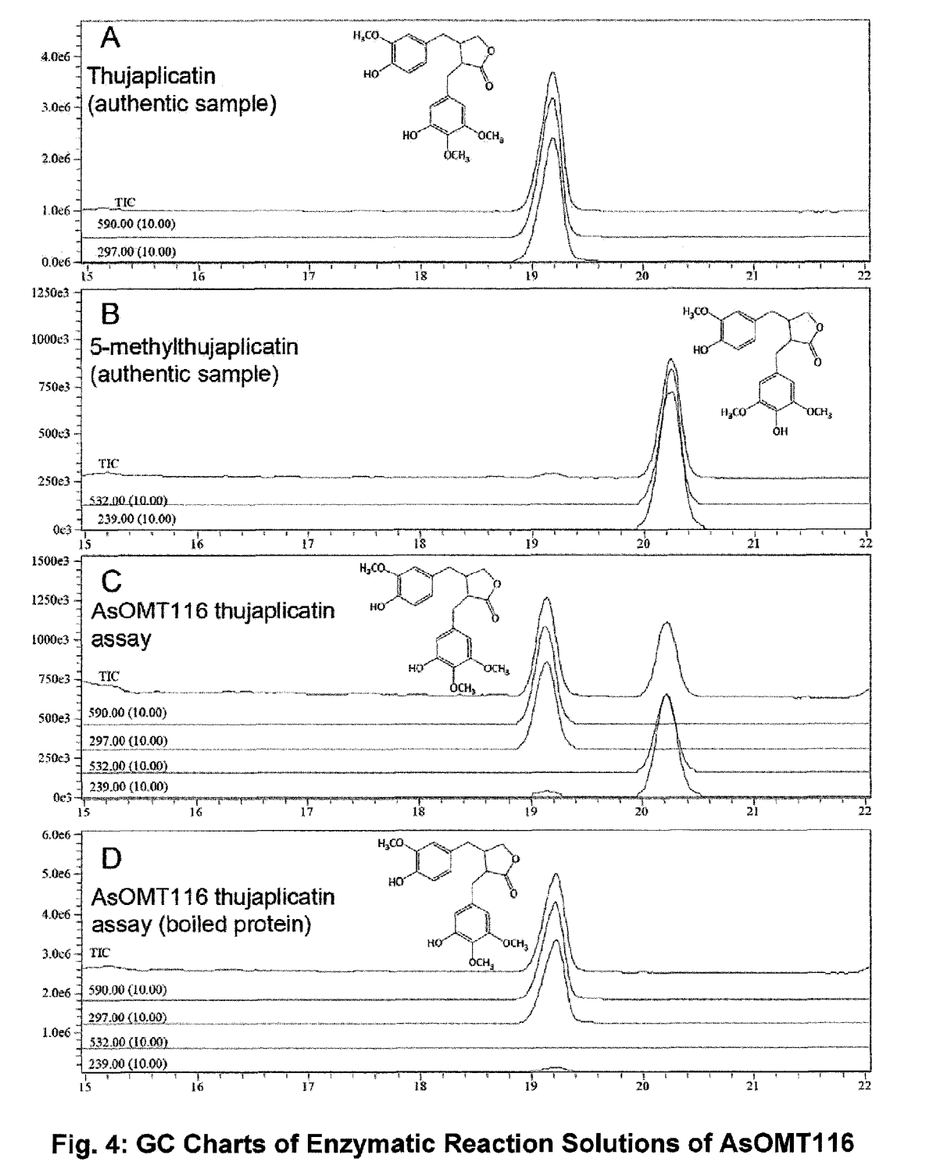
FIG. 4 shows GC-MS charts of (A) authentic thujaplicatin sample, (B) authentic 5-methylthujaplicatin sample, (C) reaction solution of methylthujaplicatin with AsOMT116 and (D) reaction solution of methylthujaplicatin with boiled AsOMT116, respectively. TIC stands for Total Ion Chromatogram.

Under the GC-MS analysis conditions described above, the enzymatic reaction solution of AsOMT116 was provided for GC-MS analysis, and a novel product was detected at retention time of approximately 20.3 minutes (FIGS. 4A and C). The peak at GC retention time of 20.3 minutes was not detected with AsOMT116 (FIG. 4D). It was thus confirmed that the peak at 20.3 minutes represents the reaction product of AsOMT116.

Figure 5:
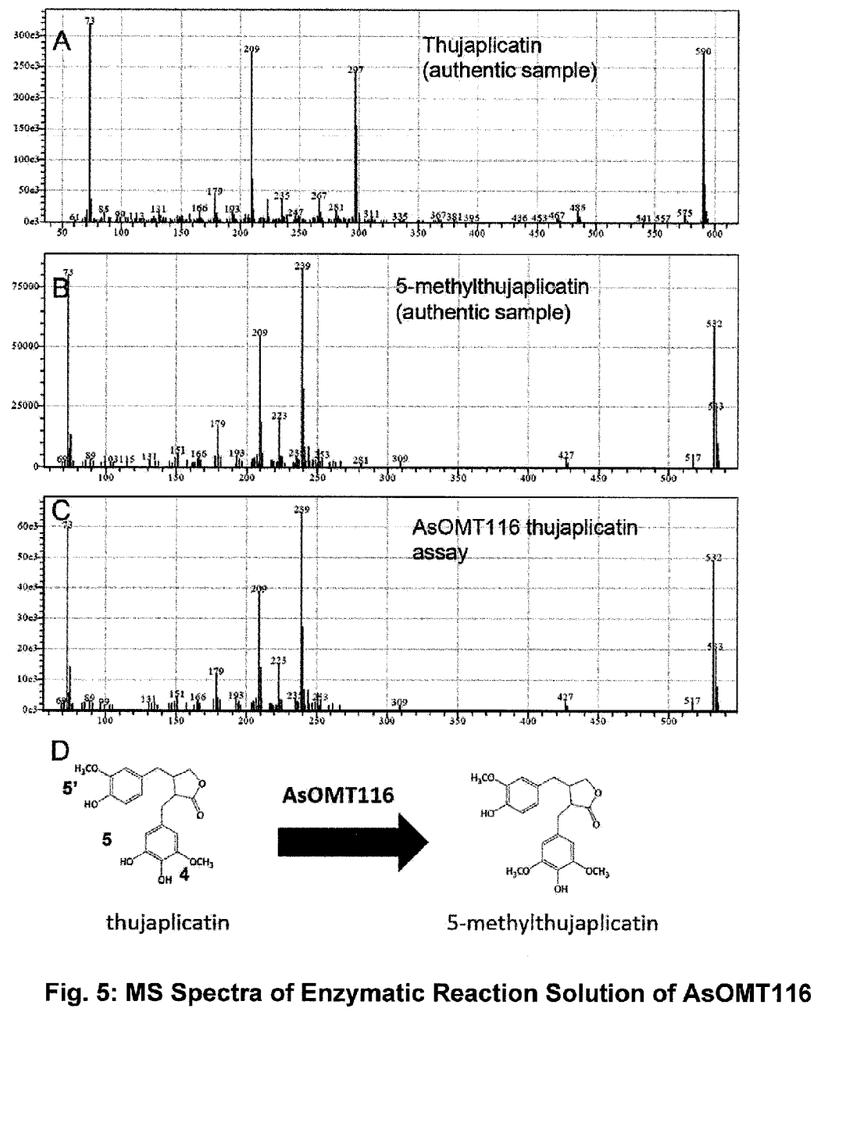
FIG. 5 shows (A) MS spectra of authentic sample methylthujaplicatin as a substrate, (B) MS spectra of authentic sample 5-methylthujaplicatin, (C) MS spectra of the reaction product of methylthujaplicatin with AsOMT116 and (D) schematic diagram of lignan methylation catalyzed by AsOMT116, respectively.

Mass spectrometric patterns of the fragment ion at 239, etc., which are common to 5-methylthujaplicatin, were detected from the results of mass spectrometry (MS) for the peak product with GC retention time of 20.3 minutes (FIGS. 5B and C). This new product in the AsOMT116 enzymatic reaction solution was found to be 5-methylthujaplicatin (FIG. 5). In thujaplicatin which is the reaction substrate, its parent ion was observed at 590 but the ion at 239 detected in FIGS. 5B and C was not observed (FIG. 5A). On the other hand, in 5-methylthujaplicatin or the reaction product, the ion at 297 detected with thujaplicatin as the reaction substrate disappeared coincident with the appearance of the fragment ion at 239 (FIGS. 5B and C). That is, the fragment ion at 239 was shown to be a fragment containing the fragment methylated by AsOMT116. It was thus confirmed by the GC-MS analysis that 5-methylthujaplicatin was the reaction product of AsOMT116.

The foregoing results demonstrate that AsOMT116 is a novel methyltransferase which specifically methylates the 5-position of thujaplicatin derived from Anthrissus sylvestris.

INDUSTRIAL APPLICABILITY

According to the present invention, lignans including thujaplicatin, etc. can be methylated and therefore, the present invention is useful in searching lignan compounds having new functions. Compounds searched using the gene of the invention or compounds obtained therefrom as intermediates may be used as active ingredients of drugs, functional food materials and molecules for new flower colors in horticultural plants. For example, methylthujaplicatin obtained in EXAMPLES described below is useful as an intermediate of podophyllotoxin known as an anticancer agent. Therefore, the present invention is useful in medical industries, food industries, agriculture, etc.

SEQ ID NO: 1: cDNA sequence of AsOMT116
SEQ ID NO: 2: amino acid sequence of AsOMT116

The invention claimed is:

1. An isolated polynucleotide selected from the group consisting of (a) to (d) below:
   (a) an isolated polynucleotide comprising the nucleotide sequence of SEQ ID NO: 1;
   (b) an isolated polynucleotide encoding a methyltransferase consisting of the amino acid sequence of SEQ ID NO: 2;
   (c) an isolated polynucleotide encoding a methyltransferase consisting of an amino acid sequence wherein 1 to 50 amino acids are deleted, substituted, inserted and/or added in the amino acid sequence of SEQ ID NO: 2, and having as lignan methylation activity; and,
   (d) an isolated polynucleotide encoding a methyltransferase having an amino acid sequence having at least 85% identity to the amino acid sequence of SEQ ID NO: 2, and having a lignan methylation activity.

2. The polynucleotide according to claim 1, which is selected from the group consisting of (g) and (h) below:
   (g) an isolated polynucleotide encoding a methyltransferase consisting of the amino acid sequence of SEQ ID NO: 2 or an amino acid sequence wherein 1 to 15 amino acids are deleted, substituted, inserted and/or added in the amino acid sequence of SEQ ID NO: 2, and having a lignan methylation activity; and,
   (h) an isolated polynucleotide encoding, a methyltransferase having an amino acid sequence having at least 85% identity to the amino acid sequence of SEQ ID NO: 2, and having a lignan methylation activity.

3. The polynucleotide according to claim 1, comprising the nucleotide sequence of SEQ ID NO: 1.

4. The polynucleotide according to claim 1, encoding a methyltransferase consisting of the amino acid sequence of SEQ ID NO: 2.

5. The polynucleotide according to claim 1, which is a DNA.

6. An isolated methyltransferase encoded by the polynucleotide according to claim 1.

7. A vector comprising the polynucleotide according to claim 1.

8. A non-human transformant introduced with the polynucleotide according to claim 1.

9. A non-human transformant introduced with the vector according to claim 7.

10. A method for producing a methyltransferase having a lignan methylation activity, which comprises culturing or growing the transformant according to claim 8 and collecting said protein from the transformant.

11. The method according to claim 10, wherein the transformant is Sesamum indicum, Forsythia intermedia or Linum usitatissimum transformed by, the polynucleotide.

12. A method for producing a methylated lignan, comprising culturing or growing the transformant according to claim 8 to produce the methyltransferase having a lignan methylation activity under conditions suitable to bring the methyltransferase with methylation activity in contact with a lignan, and collecting the methylated lignan from the transformant.

13. The method according to claim 12, wherein the transformant is Sesamum indicum, Forsythia intermedia, or Linum usitatissimum transformed by the polynucleotide.

* * * * *